(12) United States Patent
Ossepian

(10) Patent No.: US 6,216,705 B1
(45) Date of Patent: Apr. 17, 2001

(54) SMOKING ARTICLE NOT HAVING A SOLID SUBSTANCE

(76) Inventor: Gricha Ossepian, 17940 Ingomar St., Reseda, CA (US) 91335

( * ) Notice: Subject to any disclaimer, the term of this patent is extended or adjusted under 35 U.S.C. 154(b) by 0 days.

(21) Appl. No.: 09/337,314

(22) Filed: Jun. 22, 1999

(51) Int. Cl.⁷ .............................. A24F 47/00; A24F 5/04; A24F 1/02; A24F 13/04; A61M 16/00
(52) U.S. Cl. .................. 131/273; 131/198.2; 131/198.1; 131/215.1; 131/215.3; 131/272; 128/202.21
(58) Field of Search ................. 131/198.2, 273, 131/272, 198.1, 215.1, 215.3; 128/202.21

(56) References Cited

U.S. PATENT DOCUMENTS

| | | | |
|---|---|---|---|
| 198,341 | * | 12/1877 | Brisbane . |
| 1,885,689 | * | 11/1932 | Dorschel . |
| 2,850,021 | * | 9/1958 | Davis . |
| 3,200,819 | * | 8/1965 | Gilbert . |
| 3,320,953 | * | 5/1967 | Rindner . |
| 3,365,102 | * | 1/1968 | Castleberry . |
| 3,631,856 | * | 1/1972 | Taylor ........................... 128/202.21 |
| 3,674,037 | * | 7/1972 | Fortune . |
| 4,328,795 | * | 5/1982 | Cabaniss, III . |

* cited by examiner

Primary Examiner—James Derrington
Assistant Examiner—Dionne A. Walls
(74) Attorney, Agent, or Firm—Frank L. Zugelter

(57) ABSTRACT

A smoking vessel (10) constructed as a tube (11) and a mouthpiece (12) mounted at its one end, a pervious or permeable member (26) therewithin, and a valve-mechanism or assembly (15) at its other end (14) for introduction of a quantity of smoke to be disposed in the tubes' chamber (18) under pressure. A plug (34) mounted in the mouthpiece (12) closes off the neck (20) of tube (16), and includes bores (36) which abut the thickness (t) forming the neck (20). When mouthpiece (12) is unthreaded from neck (20), plug (34) disengages from the neck (20) and the pressurized smoke flows from chamber (18) through the permeable member 26 and into the mouthpiece (12) through bores (36) in plug (34), and thence inhaled by the smoker. The valve-mechanism or assembly (15) at end (14) of vessel (10) provides for introduction into chamber (18) of a quantity of smoke that is pressurized therein.

17 Claims, 1 Drawing Sheet

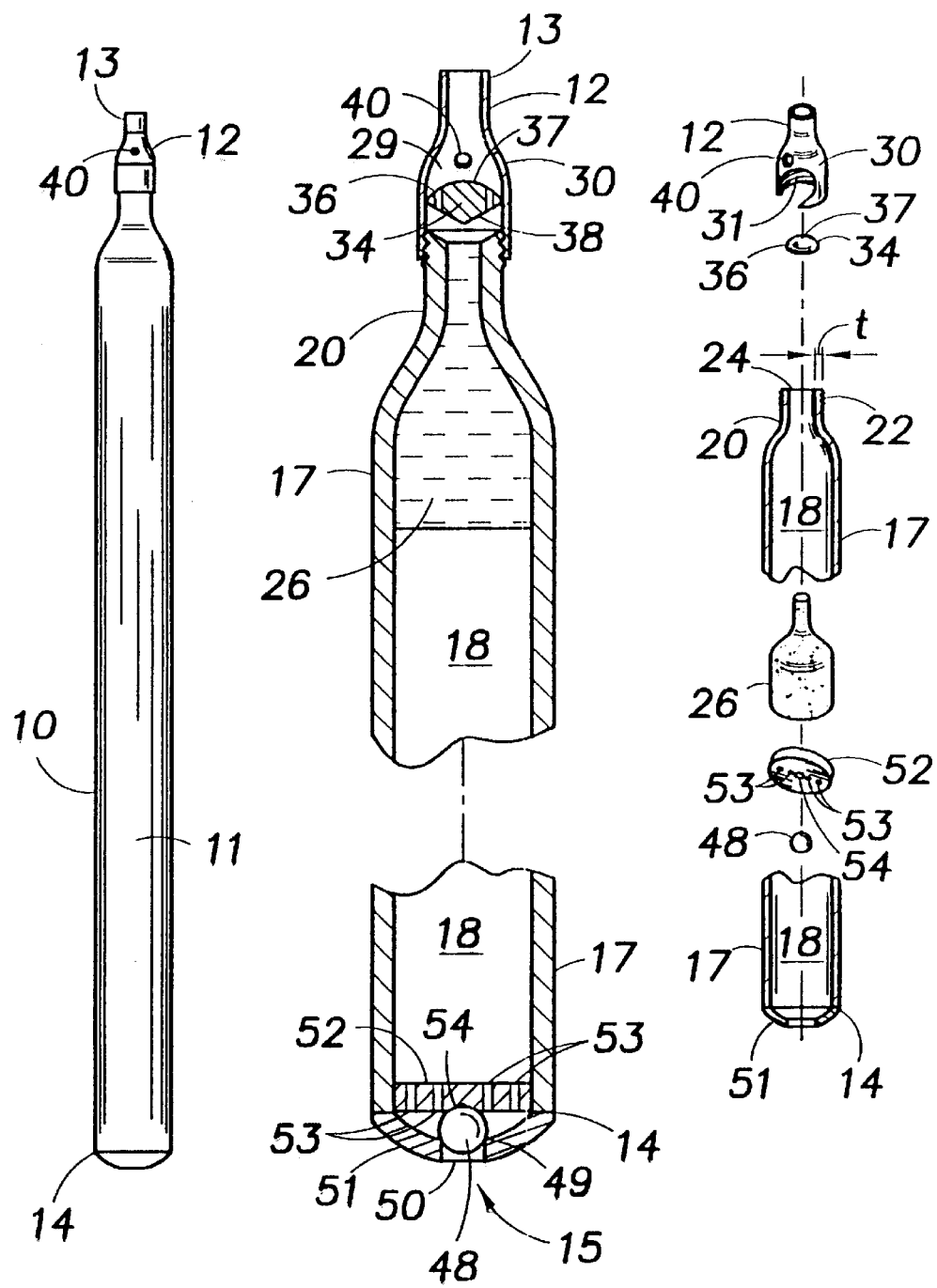

_US 6,216,705 B1_

SMOKING ARTICLE NOT HAVING A SOLID SUBSTANCE

TECHNICAL FIELD

This invention is directed to an article that can be smoked in a manner similar to smoking a cigarette, cigar, or pipe, however, without the utilization of tobacco or other solid substances therein, and in particular, is directed to a vessel that contains smoke alone, under compression, and Favorable to the senses of smell and taste, and which is inhaled by the user.

BACKGROUND TO THE INVENTION

Although the prior art discloses articles through which smoke from tobacco or non-tobacco solid substances is inhaled by the user or smoker, this inventive concept to the knowledge of the inventor is not taught or suggested by the prior art. Examples of prior art teachings known to the inventor are found in the following U.S. Pat. Nos: 198,341; 3,200,819; 3,320,953; 3,365,102; 3,674,037; 4,328,795; 4,813,438; and 5,150,724.

SUMMARY OF THE INVENTION

The inventive concept is directed to a vessel, such as a tubular member, having a chamber that contains a quantity of pressurized smoke, of a tobacco flavor or one or more other flavors pleasant to the human senses of smell and taste, and a mouthpiece through which the smoke is inhaled by the user or smoker. A pervious or permeable member is included in the vessel for controlling the flow of pressurized smoke that is to be inhaled, and a valve mechanism or assembly is provided at its other end, or elsewhere of the vessel, and by which smoke is introduced into the chamber and pressurized therein to fill up the chamber with a quantity of smoke under compression. The mouthpiece includes a plug having bores which engage or abut the thickness of and at the end of the wall(s) under the mouthpiece of the tube forming the vessel. The mouthpiece and tube are axially adjustable to one another so that by such adjustable connection, for example, by threaded means, the bored plug displaces to and from the tube's end to provide egress of the chambers smoke into and through its bores into the mouthpiece. Such adjustability provides the smoker of the amount of smoke intake from the mouthpiece as desired. The mouthpiece itself includes an airhole for admission of air that then is mixed with the smoke flowing through the mouthpiece to its tip at which the resulting mixture is inhaled into the mouth of the smoker.

An object of this invention is to provide a novel smoking article in which tobacco is not necessary.

Another object of the invention is to provide for the introduction of air into the article for mixing with, to a desired extent, the smoke to be inhaled.

A further object of the invention is to provide an enjoyable smoking article without the presence of nicotine or carcinogenic materials that are usually associated with tobacco and/or its smoke.

A still further object of the invention is to eliminate the danger of a smoke containing carcinogenic materials or products from entering the atmosphere and environment, and which could hinder the health of a person exposed to such materials or products.

A yet further object of this invention is to provide a personal enjoyment and satisfaction to the user in terms of the user's senses of taste and smell.

These and other objects and advantages will become more apparent upon a full and complete reading of the following description, its appended claims, and the accompanying drawing comprising one (1) sheet of three (3) FIGURES.

BRIEF DESCRIPTION OF THE DRAWING

FIG. 1 is a full view of an article embodying the invention.

FIG. 2 is an enlarged cross-sectional view, a portion omitted, of the article of FIG. 1.

FIG. 3 is an exploded perspective view, portions omitted, of FIGS. 1 and 2.

PREFERRED EMBODIMENT OF CARRYING OUT THE INVENTION

Referring now to the drawing wherein the following numerals correspond to the reference characters in the FIGURES therein, FIG. 1 illustrates a vessel or article 10, in the form of a tube 11. A mouthpiece 12 having a tip 13 is adjustably mounted at the tube's one end while adjacent to or at its other end 14 a valve mechanism or assembly 15, FIGS. 2 and 3, is securely fixed or mounted thereto.

Tube 11 is formed by one or more walls 17, preferably of circular configuration, for embracing a chamber 18 into which a quantity of pressurized smoke (to be inhaled), not illustrated, is to be disposed under pressure. The wall 17 is reduced at its neck 20, and on which reduction exteriorly mounted threads 22 about the tube's wall 17 are formed, while neck 20 retains an opening 24 smaller in its dimensions than that of chamber 18 with which opening 24 communicates. A pervious or permeable member 26 for controlling the amount of smoke as it flows from chamber 18 into the volumetric dimension of neck 20, is suitably securely mounted in tube 11 co-extensively in its dimensions to the portions of chamber 18 and to the reduced dimensions, if any, of neck 20 in which it can be situated.

The oral mouthpiece or stem 12, contains its own chamber 29, FIG. 2, formed by its own walled formation 30. Wall formation 30 includes internally mounted threads 31 in its bottom portion, and is adjustably mounted to tube 11 by the cooperative rotating action of the pair of threads 31, 22. A plug 34, including one or more bores 36 extending throughout its body from its upper wall 37 to its bottom wall 38, is suitably securely mounted within and to the mouthpiece 12. Plug 34 displaces to and from opening 24 of neck 20 upon the relative rotation between the mouthpiece 12 and the neck 20, by the turning of the cooperating sets of threads 31, 22, one to or against the other. Bores 36 are positioned in the formation of plug 34 to be in alignment with a thickness t forming the reduced neck 20. Thus, as bottom wall 38 on plug 34 engages or abuts thickness t, the quantity of smoke in chamber 18 cannot flow into mouthpiece 12. When bottom wall 38 disengages from the thickness t of the tube's wall 17, a quantity of pressurized smoke can flow from chamber 18 through the pervious membrane 26 into the mouthpiece 12. A hole 40 is included in the wall formation 30 for mouthpiece 12, above plug 34, for ingress of air into it for mixing with smoke that is drawn into mouthpiece 12 by the inhalation provided by the smoker at the lip-or-teeth-engaging portion or tip 13 included in the mouthpiece 12.

The valve mechanism or assembly 15 is securely mounted to vessel 10 at its end 14. This mechanism or assembly 15 includes a valve-member 48, illustrated in the FIGURES as a spherical ball, mounted on its seat 49 formed by an opening 50 in a body formation 51 that is preferably press-fit at the end 14 to the tube 11. A disc 52 of sufficient thickness so as to retain positive contact with wall 17, i.e., not to twist about in its tube position, and including one or more bores 53 through which quantities of smoke flow to above the disc 52, is slidably mounted in chamber 18, and maintains force directly upon valve member 48 and against its seat 49 under the condition that exists when the chamber 18 is filled with smoke that is pressurized within tube 11, and while or whether plug 34 is displaced to or away from the opening 24 in the neck 20. A void or niche 54, FIG. 2, is formed in general alignment with opening 50 to maintain ball 48 over opening 50 and which prevents ball 48 from straying from its engagement with seat 49.

In operation, chamber 18 of vessel 10, is filled with a quantity of pressurized smoke through the valve member 48, while plug 34 is displaced against the thickness t of neck 20, and the bores 36 abut thickness t. A way of smoking article 10 by a person can be accomplished in the following manner. The teeth-engaging portion or tip 13 of the mouthpiece 12 is held between the teeth of the user who then rotates the threads 22 on tube 11 against the threads 31 on the mouthpiece 12, the plug 34 displacing from the thickness t of neck 20. The bores 36 in plug 34 become disengaged from the thickness t. The pressurized smoke in chamber 18 now flows through the pervious or permeable member 26 into and through bores 36 of plug 34 and into the chamber 29 of the mouthpiece 12, to be mixed with air ingressing through aperture 40 of mouthpiece 12. The smoker determines how fast or slow the flow of the pressurized smoke ingresses into mouthpiece 12 and into mouth, by reason of the amount of rotation of tube 11 from mouthpiece 12 and by its tip 13 that is being held by the teeth of the smoker. Rotation of tube 11 relative to the mouthpiece 12 adjusts the quickness of flow of smoke from chamber 18 through the member 26 into the mouthpiece 12, depending upon the pull of smoke desired in the inhalation step by the smoker, and so chosen by the smoker by such relative rotation, using the senses of taste flowing into the human's mouth and/or by the smell of the smoke to adjust such relative rotation to a desired position.

A smoke-carrying container that is capable of discharging smoke and introducing such smoke into vessel 10 is not illustrated, however, such a container with a valving mechanism, much like the kind associated with and including a needle for introduction of pressurized air into a valve stem on a vehicular tire, is utilized to introduce through the valve mechanism or assembly 15 the smoke to be accumulated and pressurized in chamber 18. Such a needle in its insertion into opening 50 raises the valve-member 48 from its seat 49 as disc 52 slides upwardly, thereby introducing smoke carried by the actuated container into chamber 18, into its volumetric dimension below and above bored disc 52, filling the chamber up to a pressurized state or condition by operation of the discharging smoke-filled container. Upon filling vessel 10, the noted needle is removed from opening 50, the valve-member 48 returning to set upon opening 50 by reason of the pressure of the quantity of smoke in chamber 18, thereby sealing off vessel 10. Article 10 now is in a condition or state for smoking.

The materials of the vessel 10 and mouthpiece 12 may be of plastic, metal, wood, or other suitable materials for constructing the tube 11. The pervious or permeable member 26 is of suitable known substance, such as sponge-like material. The remaining elements may be formed of commonly-used and suitable plastic or metal materials to effect a practical assembly of article 10 for an efficient operation in "smoking the article", to the personal satisfaction of its user, who relies on a personal sense of taste and smell from the smoke of article 10, to enjoying it as an activity or as a habit.

In assembly of the tube 11, tube 11 being first fabricated to include threads 22, neck 20 if desired, and open end 14, member 26 is introduced through open end 14 and suitably fixedly installed as illustrated in FIG. 2. Bored disc 52 is inserted into tube 11, for slidable movement, followed by valve ball 48 that is positioned on its niche 54. Thereafter, body formation 51 with its opening 50 is press fit at the end 14 to the walls 17 of tube 11. Plug 34 is suitably affixed within the fabricated mouthpiece 12 to the latter's wall 38, before or after it is threaded, taking into account such affixation providing for the maximum extent of displacement of the plug 34 from its engagement with neck 20 without mouthpiece 12 disengaging from neck 20 or tube 11. Fabricated mouthpiece 12 includes its air-hole 40.

Various modifications and changes may be included within article 10, without changing the scope or spirit of its invention or inventive concept, and the purpose of the above description is to illustrate the preferred embodiment and is not intended as a limitation upon the claims. For example, mouthpiece 12 and tube 11 may be constructed in any desired geometrical configurations, and possibly integrally as well. The threads 22 and 31 can be located on the reversed surfaces of their corresponding elements 17 and 30. Mouthpiece 12 need not include an air-hole 40. The invention is not limited to the narrowing of tube 11 to form a neck 20. The pervious or permeable member 26 may be situated within the tube 11 other than as illustrated as being situated between neck and chamber. Also, member 26 need not be included. Tube 11 is not limited to a circular or circumferential configuration as illustrated.

INDUSTRIAL APPLICABILITY

The subject matter of the article is applicable to the tobacco smoking industry, to the/an industry in which persons seeking to stop smoking tobacco products can be classified, and to an industry fashioned on the merits of the disclosed inventive concept.

Therefor, what I claim to be novel and patentably distinct is:

1. A vessel as an article of manufacture for smoking comprising:
   a tube having wall means having a thickness embracing a chamber and with opposing ends,
   a mouthpiece adjustably mounted on said tube at one of its ends,
   plug means having bore means therein in alignment with the thickness of said wall means, and
   valve means mounted at the other of said ends of said tube,
whereby when a quantity of smoke is introduced through said valve means into the chamber for pressurization therein, such smoke is flowable into said mouthpiece through said bore means upon adjusting said mouthpiece in relation to said wall means.

2. The vessel of claim 1 including means mounted in said tube for controlling the flow of smoke from the chamber into the mouthpiece.

3. The vessel of claim 2 wherein said controlling means comprises
   a permeable member fixed in said chamber and through which pressurized smoke flows from said chamber therethrough to said plug means.

4. The vessel of claim 1 or claim 2 or claim 3 wherein said valve means comprises
   a bored disc slidably mounted in the chamber adjacent the other of said ends, a body formation including an opening and being securely mounted to said other of said ends, and a valve member seated against such opening in said body formation, whereby upon smoke being introduced into the chamber said bored disc maintains said valve member against the opening.

5. The vessel of claim 1 or claim 2 or claim 3 including a hole in said mouthpiece for ingress of air.

6. The vessel of claim 1 or claim 2 or claim 3 including a neck formed in said tube, said mouthpiece mounted to said neck.

7. The vessel of claim 1 or claim 2 or claim 3 including a hole in said mouthpiece for ingress of air and a neck formed in said tube, said mouthpiece mounted to said neck.

8. The vessel of claim 1 or claim 2 or claim 3 including means for adjusting said mouthpiece to said tube whereby they displace towards and away from each other and in so doing said bore means in said plug correspondingly engages and disengages from said wall means.

9. The vessel of claim 8 wherein said adjusting means comprises cooperating threads on said mouthpiece and said tube.

10. The vessel of claim 9 wherein said valve means comprises a bored disc slidably mounted in the chamber adjacent the other of said ends, a body formation forming an opening and being securely mounted to said other of said ends, and a valve member seated against such opening by means of said bored disc.

11. The vessel of claim 10 including a hole in said mouthpiece for ingress of air.

12. The vessel of claim 10 including a neck formed in said tube, said mouthpiece adjustably mounted to said neck.

13. The vessel of claim 10 a hole in said mouthpiece for ingress of air, and a neck formed in said tube, said mouthpiece adjustably mounted to said neck.

14. The vessel of claim 4 including a niche in said bored disc for aligning said valve member with said opening.

15. The vessel of claim 14 including a neck formed in said tube, said mouthpiece mounted to said neck.

16. The vessel of claim 14 including a hole in said mouthpiece for ingress of air.

17. The vessel of claim 14 including a hole in said mouthpiece for ingress of air and a neck formed in said tube, said mouthpiece mounted to said neck.

* * * * *

UNITED STATES PATENT AND TRADEMARK OFFICE
CERTIFICATE OF CORRECTION

PATENT NO. : 6,216,705 B1
DATED : April 17, 2001
INVENTOR(S) : Oseppian, Gricha

It is certified that error appears in the above-identified patent and that said Letters Patent is hereby corrected as shown below:

<u>Title page,</u>
Item [76], the corrected spelling of the inventor is to be read as
-- Gricha Oseppian --.

Signed and Sealed this

Sixth Day of November, 2001

Attest:

*Nicholas P. Godici*

NICHOLAS P. GODICI
*Attesting Officer*     *Acting Director of the United States Patent and Trademark Office*